(12) United States Patent
Yamamoto et al.

(10) Patent No.: US 8,003,092 B2
(45) Date of Patent: Aug. 23, 2011

(54) ANTIALLERGIC AGENT, UTILIZATION THEREOF FOR REDUCING ALLERGY AND METHOD OF REDUCING ALLERGY

(75) Inventors: Naoyuki Yamamoto, Sagamihara (JP); Yuu Ishida, Machida (JP); Izuki Bando, Yamato (JP)

(73) Assignee: Calpis Co., Ltd., Tokyo (JP)

( * ) Notice: Subject to any disclaimer, the term of this patent is extended or adjusted under 35 U.S.C. 154(b) by 111 days.

(21) Appl. No.: 12/253,819

(22) Filed: Oct. 17, 2008

(65) Prior Publication Data

US 2009/0047264 A1 Feb. 19, 2009

Related U.S. Application Data

(63) Continuation of application No. 10/518,801, filed as application No. PCT/JP03/08094 on Jun. 26, 2003, now abandoned.

(30) Foreign Application Priority Data

Jun. 26, 2002 (JP) ................................. 2002-185897

(51) Int. Cl.
*A01N 63/00* (2006.01)
*C12N 1/20* (2006.01)
(52) U.S. Cl. ...................... 424/93.45; 424/93.4; 435/854
(58) Field of Classification Search .......................... None
See application file for complete search history.

(56) References Cited

U.S. PATENT DOCUMENTS

| 5,516,684 | A | * | 5/1996 | Saito et al. ................. 435/252.9 |
| 5,707,854 | A | | 1/1998 | Saito et al. |
| 2003/0157079 | A1 | | 8/2003 | Kato et al. |

FOREIGN PATENT DOCUMENTS

| DE | 20202562 | 5/2002 |
| JP | 62130679 | 6/1987 |
| JP | 09002959 | 1/1997 |
| JP | 10114667 | 5/1998 |
| JP | 10309178 | 11/1998 |
| JP | 2000086524 | 3/2000 |
| JP | 2000095697 | 4/2000 |
| JP | 2000239175 | 9/2000 |
| WO | WO-9514485 | 6/1995 |
| WO | WO-0137865 | 5/2001 |
| WO | WO-0197822 | 12/2001 |
| WO | WO-0216554 | 2/2002 |

OTHER PUBLICATIONS

Takashi Nakamura et al., "*Lactobacillus acidophilus*L92 Kabu no Keiko Toyo ga Mouse Kesseichu no Ranpaku Albumin Tokuiteki IgE Kotai Revel ni Oyobosu Eikyo", Japan Society of Bioscience, Biotechnology, and Agrochemistry Taikai Koen Yoshishu, Mar. 2003, vol. 2003, p. 75.

Suguru Ishida et al., "*Lactobacillus acidophilus*L92 Kabu Hakkonyu no Sesshu ni yoru Kafunsho Shojo Kaizen Sayo no Kensho", Japan Society for Bioscience, Biotechnology and Agrochemistry Taikai Koen Yoshishu, Mar. 2003, vol. 2003, p. 75.

Database TCM, SIPO; Taketoshi Yamada: Antiallergic Composition, Oct. 18, 1995, XP002428472.

Hilton et al., Ingestion of Yogurt Containing *Lactobacillus acidophilus*as Prophylaxis for Candidal Vaginitis, Annals of Internal Medicine, vol. 116, No. 5, pp. 353-357, Mar. 1992, X002086393.

Sepp et al., Intestinal *Lactobacilli*of Estonian and Swedish Children, Microbial Ecology in Health and Disease, vol. 14, pp. 75-80, 2002, XP009081321.

T. Matsuzaki et al., "The Effect of Oral Feeding of *Lactobacillus casei*Strain Shirota on Immunoglobulin E Production in Mice", J Dairy Sci: 81:48-53, 1998.

Shinji Murosaki et al., "Heat-killed *Lactobacillus plantarum*L-137 suppresses naturally fed antigen-specific IgE production by stimulation of IL-12 production in mice." J Allergy Clin Immunol, Jul. 1998 vol. 102, p. 57-64.

* cited by examiner

*Primary Examiner* — Vera Afremova
(74) *Attorney, Agent, or Firm* — Fish & Richardson P.C.

(57) ABSTRACT

The present invention provides an antiallergic agent containing, as an active ingredient, lactic acid bacteria selected from the group consisting of lactic acid bacteria of the species *Lactobacillus acidophilus, Lactobacillus fermentum*, and combinations thereof. The antiallergic agent is capable of improving allergic diathesis by reducing the IgE level, which is contributive to development of Type I allergy, and is easy to take and highly safe. The present invention also provides use of the antiallergic agent for reducing allergy, and a method for reducing allergy using the antiallergic agent.

11 Claims, 6 Drawing Sheets

\*\*: p<0.01 with respect to non-fermented skim milk

ANTIALLERGIC AGENT, UTILIZATION THEREOF FOR REDUCING ALLERGY AND METHOD OF REDUCING ALLERGY

The present application is a continuation of U.S. patent application Ser. No. 10/518,801, filed Jan. 26, 2005, which is a National phase of International Patent Application Ser. No. PCT/JP03/08094, filed Jun. 26, 2003, which claims the benefit of Japanese Patent Application Serial No. 2002-185897, filed Jun. 26 2002, all of which are hereby incorporated by reference in their entireties.

FIELD OF ART

The present invention relates antiallergic agents. The invention also relates to use of the antiallergic agents for reducing allergy, and a method for reducing allergy.

BACKGROUND ART

Allergic patients have been increasing in number every year in many countries including Japan, and high incident of allergic adults, one out of three in Japan, is reported. Allergic diseases are categorized into four types, type I to IV, depending on their mechanism of action. Some kinds of allergic rhinitis such as pollinosis, bronchial asthma, and atopic dermatitis are Type I immunoglobulin E (IgE)-mediated allergy, wherein increase in antigen-specific IgE level in blood enhances the risk of developing allergic symptoms.

The mechanism of development of Type I allergy is as follows. When an antigen, such as pollens, house dust, or mites, invades the body, an IgE antibody specific to such antigen is produced, and binds to mast cells or Fcε receptors on the basophil surface to sensitize the subject. When the antigen further invades the body, the antigen binds to the IgE antibody to form a complex. This causes degranulation, wherein chemical mediators in the granules, such as histamine and leukotoriene, are released to develop allergic symptoms.

Recently, allergic diseases are treated mainly with antagonists to chemical mediators, such as antihistamine, and steroids used as anti-inflammatory agents. However, both of these agents merely provide symptomatic therapy, and steroids inhibit the overall immune response, resulting in side effects. Alternatively, agents for inhibiting release of chemical mediators by inhibition of degranulation are also used, but no fundamental therapeutic agents have not been found for specifically reducing the IgE antibody, which is the major factor of allergy development.

Further, for necessary chronical administration, antiallergic agents that are easy to take and highly safe are desired. Accordingly, novel antiallergic agents having such properties are demanded.

SUMMARY OF THE INVENTION

It is an object of the present invention to provide an antiallergic agent that is capable of improving allergic diathesis by reducing the IgE level, which is contributive to development of Type I allergy, and that is easy to take and highly safe, as well as a method for reducing allergy.

In order to achieve the above object, the present inventors have constructed a mouse model wherein the antigen-specific IgE level has remarkably been elevated without substantial increase in the IgG level. Using this model, the inventors have made researches on IgE-level repressing effect of various lactic acid bacterial strains that may affect the intestinal immune system, to find out that, among the various tested lactic acid bacteria, certain bacteria have a particularly excellent inhibitory effect on IgE production, thereby completing the present invention.

According to the present invention, there is provided an antiallergic agent comprising, as an active ingredient, lactic acid bacteria selected from the group consisting of lactic acid bacteria of the species *Lactobacillus acidophilus*, lactic acid bacteria of the species *Lactobacillus fermentum*, and combinations thereof.

According to the present invention, there is also provided the antiallergic agent mentioned above, wherein said lactic acid bacteria of the species *Lactobacillus acidophilus* are bacteria of the strain selected from the group consisting of *Lactobacillus acidophilus* CL0062 (deposited at International Patent Organism Depositary, FERM BP-4980), *Lactobacillus acidophilus* CL92 (deposited at International Patent Organism Depositary, FERM BP-4981), and combinations thereof.

According to the present invention, there is also provided the antiallergic agent mentioned above, wherein said lactic acid bacteria of the species *Lactobacillus fermentum* are of the strain *Lactobacillus fermentum* CP34 (deposited at International Patent Organism Depositary, FERM BP-8383).

According to the present invention, there is further provided the antiallergic agent mentioned above, which reduces, when administered orally, antigen-specific IgE level in blood in a mouse rhinitis model wherein antigen-specific IgE level in blood has been elevated by nasally exposing the mouse to continuous antigen stimulation.

According to the present invention, there is also provided use of the particular lactic acid bacteria mentioned above in the manufacture of a medicament for reducing allergy.

According to the present invention, there is further provided a method for reducing allergy comprising administering an effective dose of the antiallergic agent mentioned above to a subject in need of such reduction.

EMBODIMENTS OF THE INVENTION

The antiallergic agent according to the present invention contains, as an active ingredient, lactic acid bacteria selected from the group consisting of lactic acid bacteria of the species *Lactobacillus acidophillus*, lactic acid bacteria of the species *Lactobacillus fermentum*, and combinations thereof.

The lactic acid bacteria of the species *Lactobacillus acidophilus* may particularly preferably be of the strain *Lacto-* bacillus acidophilus CL0062 (deposited at International Patent Organism Depositary of Central 6, 1-1-1 Higashi, Tsukuba, Ibaraki, Japan, under the deposit number FERM BP-4980 on Mar. 4, 1994), the strain *Lactobacillus acidophilus* CL92 (deposited at International Patent Organism Depositary under the deposit number FERM BP-4981 on Mar. 4, 1994), or a combination of these. The lactic acid bacteria of the species *Lactobacillus fermentum* may particularly preferably be of the strain *Lactobacillus fermentum* CP34 (deposited at International Patent Organism Depositary under the deposit number FERM BP-8383 on May 23, 2002). These three bacterial strains have been deposited under the Budapest Treaty on the International Recognition of the Deposit of Microorganisms for the Purposes of Patent Procedure. All restrictions on the availability to the public of *Lactobacillus fermentum* CP34 strain will be irrevocably removed upon the granting of a patent. *Lactobacillus acidophilus* CL0062 and CL92 strains are already available to public.

*Lactobacillus acidophilus* CL0062 strain has the following bacteriological properties:
(Morphological Properties)
1) Shape of Cell; rod,
2) Motility; none,
3) Spore Formation; none,
4) Gram Stain; positive
(Physiological Properties)
1) Catalase Production; negative,
2) Indole Production; negative,
3) Nitrate Reduction; negative,
4) Aerobic Growth; facultative anaerobic,
5) Growth at 15° C.; none,
6) Formation of DL-lactic acid from glucose by homolactic fermentation without formation of gases,
7) Formation of Acids from Carbohydrates

| | |
|---|---|
| glucose; + | melibiose; + |
| lactose; + | raffinose; + |
| mannose; + | mannitol; − |
| fructose; + | sorbitol; − |
| galactose; + | esculin; + |
| sucrose; + | salicin; + |
| arabinose; − | N-acetylglucosamine; + |
| maltose; + | amygdalin; + |
| xylose; − | gentiobiose; + |
| rhamnose; − | melezitose; − |
| cellobiose; + | dextrin; + |
| trehalose; + | starch; − |

*Lactobacillus acidophilus* CL92 strain has the following bacterial properties:
(Morphological Properties)
1) Shape of Cell; rod,
2) Motility; none,
3) Spore Formation; none,
4) Gram Stain; positive
(Physiological Properties)
1) Catalase Production; negative,
2) Indole Production; negative,
3) Nitrate Reduction; negative,
4) Aerobic Growth; facultative anaerobic,
5) Growth at 15° C.; none,
6) Formation of DL-lactic acid from glucose by homolactic fermentation without formation of gases,
7) Formation of Acids from Carbohydrates

| | |
|---|---|
| glucose; + | melibiose; − |
| lactose; + | raffinose; + |
| mannose; + | mannitol; − |
| fructose; + | sorbitol; − |
| galactose; + | esculin; + |
| sucrose; + | salicin; + |
| arabinose; − | N-acetylglucosamine; + |
| maltose; + | amygdalin; + |
| xylose; − | gentiobiose; + |
| rhamnose; − | melezitose; − |
| cellobiose; + | dextrin; − |
| trehalose; + | starch; − |

*Lactobacillus fermentum* CP34 strain has the following bacteriological properties:
(Morphological Properties)
1) Shape of Cell; rod,
2) Motility; none,
3) Spore Formation; none,
4) Gram Stain; positive
(Physiological Properties)
1) Catalase Production; negative,
2) Aerobic Growth; facultative anaerobic,
3) Formation of DL-lactic acid from glucose with formation of gases (+),
4) Carbohydrate Degradation

| | |
|---|---|
| arabinose; − | cellobiose; − |
| xylose; − | lactose; + |
| melibiose; − | trehalose; − |
| rhamnose; − | amygdalin; − |
| ribose; + | raffinose; − |
| glucose; + | melezitose; − |
| mannose; − | mannitol; − |
| fructose; + | sorbitol; − |
| sucrose; + | esculin; − |
| maltose; + | salicin; − |

The content of the above-mentioned lactic acid bacteria in the antiallergic agent of the present invention is not particularly limited, and may suitably be adjusted depending on ease of production or a preferred daily dosage. For example, when the agent is in a liquid formulation, a preferred content of the bacteria is from $1 \times 10^7$ cells/ml to $1 \times 10^{10}$ cells/ml.

The antiallergic agent of the present invention may optionally contain other components, in addition to the lactic acid bacteria. Examples of such other components may include additives such as excipients, or components of the medium to be discussed later.

The antiallergic agent of the present invention may be prepared by culturing the lactic acid bacteria in a medium.

Any medium may be used for culturing, as long as the above-mentioned lactic acid bacteria may grow therein, and animal milk, skim milk, milk whey, MRS medium, GAM medium, BL medium, Briggs Liver Broth, or other synthetic media may be used. The temperature for the culture may be 25° C. to 50° C., preferably 35° C. to 42° C. The culture time may be 3 hours to 48 hours, preferably 8 hours to 12 hours. The cultured medium may be used as the antiallergic agent of the present invention with or without further processing. For example, the bacterial cells harvested from the cultured medium by centrifugation or filtration, a lyophilized product thereof, a heat-treated product thereof, or ground bacterial cells may be used as the antiallergic agent of the present invention. Further, the bacterial cells in the above forms may further be formulated, or blended in various food materials such as beverages, tablets, pastes, or bread, before use as the antiallergic agent of the present invention.

The antiallergic agent of the present invention may be administered by any route, but oral administration is preferred. The dosage may be not lower than $2 \times 10^9$ cells per day, preferably $2 \times 10^{10}$ cells per day for oral administration to human. This dosage of agent may be administered in a single dose or in a plurality of doses per day.

The antiallergic agent of the present invention effectively suppresses the IgE level as will be demonstrated in Examples, and is expected to be highly safe since the active ingredient of this agent is bacterial cells taken as food.

The method for reducing allergy according to the present invention includes the step of administering an effective dose of the antiallergic agent mentioned above to a subject in need of such reduction. The subject may be animals such as human or other mammals.

The antiallergic agent of the present invention effectively suppresses the IgE level in living organisms, and is easy to take and highly safe. Thus the present agent is useful for suppressing allergy involving excess IgE level.

EXAMPLES

The present invention will now be explained in more detail with reference to Examples, which are illustrative only and do not intend to limit the present invention.

Example 1

(Preparation of IgE-elevated Mice)

Male BALB/c mice were obtained from Charles River Japan, and raised under free access to CE-2 (CLEA Japan, Inc.) as a feed. 10 μg of ovalbumin (abbreviated as OVA hereinbelow, manufactured by SIGMA CHEMICAL CO.) and 2 mg of aluminum hydroxide (WAKO PURE CHEMICAL INDUSTRIES, LTD.) as an adjuvant were suspended in 300 μl of saline. Ten of the above mice at six weeks old were injected intraperitoneally with this suspension on the first day of sensitization and on day 4 for primary sensitization. For secondary sensitization, the nose of each mouse was soaked in an OVA antigen solution containing 25 mg OVA/ml of saline for three seconds, and this soaking operation was repeated three times as one cycle. Two cycles of soaking operation was performed per day, and the daily soaking was performed from day 10 to day 16 to prepare IgE-elevated mice.

Figure 1:
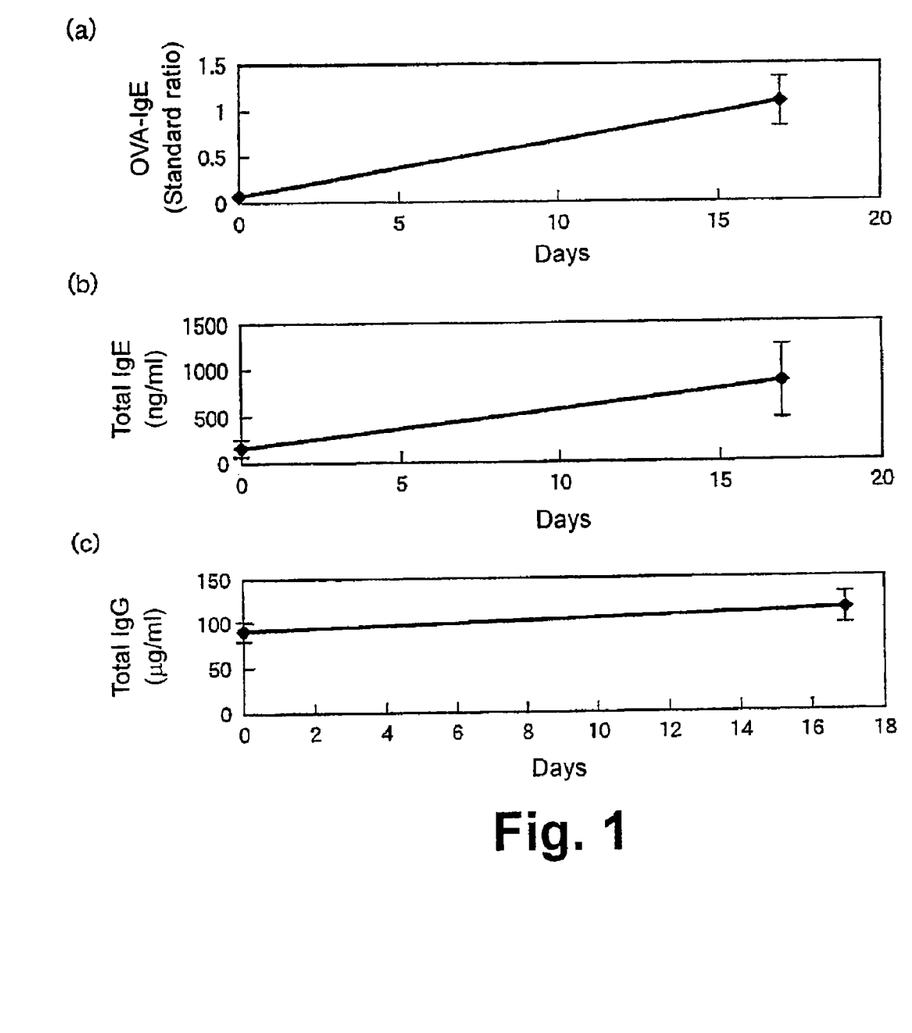
FIG. 1 shows graphs indicating the changes in immunoglobulin level in blood in IgE-elevated mice in Example 1.

Blood samples were obtained from the ophthalmic veins of the IgE-elevated mice on the first day and day 17 of sensitization, and serum samples were obtained. The OVA-specific IgE (abbreviated as OVA-IgE hereinbelow), the total IgE, and the total IgG in the serum samples were measured in accordance with the methods to be discussed below. The results are shown in FIGS. 1(a) to 1(c).

From the results shown in FIGS. 1(a) to 1(c), it is understood that the increase in total IgE and OVA-IgE levels in blood were remarkably larger than that in IgG level as a result of the sensitization. Accordingly, a mouse allergy model was constructed, wherein the IgE and the antigen-specific IgE levels in blood were elevated without change in the entire immune system.

(Measurement of Blood Ova-IgE)

The blood OVA-IgE level was measured by the sandwich ELISA. 100 μl of saline solution containing 10 μg/ml of a sheep polyclonal anti-mouse IgE antibody (trade name AAM11, manufactured by DAINIPPON PHARMACEUTICAL CO., LTD.) was added to each well of a 96-well immunoplate (manufactured by CORNING INCORPORATED), and incubated overnight at 4° C. The plate was washed three times with a phosphate buffer (containing 137 mM NaCl, 2.7 mM KCl, 8.1 mM Na$_2$HPO$_4$, and 1.5 mM KH$_2$PO$_4$, abbreviated as PBS hereinbelow), coated with 0.5% casein-PBS, and incubated for 3 hours at room temperature. After the plate was washed three times with PBS, 100 μl of a 1/10 PBS dilution of a serum sample was added to each well, and reacted overnight at 4° C. After the plate was washed four times with PBS, 100 μl of 0.5% casein-PBS solution containing 10 μg/ml of OVA that had been biotinylated using a Biotinylation kit (manufactured by AMERICAN QUALEX INTERNATIONAL INC.) (biotin-labeled OVA) was added to each well, and reacted for 2 hours at room temperature. After the plate was washed five times with PBS, 100 μl of a PBS solution containing 1 μg/ml of streptavidin-peroxidase (manufactured by SIGMA CHEMICAL Co.) and 0.5% casein was added to each well, and reacted for 1 hour at room temperature. After the plate was washed five times with 0.1%-Tween 20 in PBS, 100 μl of 0.2 M citric acid buffer (prepared by mixing 0.2 M citric acid and 0.2 M trisodium citrate and adjusting the pH to 5) containing 600 μg/ml of 2,2'-azino-bis(3-ethylbenzothiazoline-6-sulfonic acid) (abbreviated as ABTS hereinbelow, manufactured by BOEHRINGER MANNHEIM) and 0.006% hydrogen peroxide was added to each well, and shielded for 3 hours at 37° C. for coloration. After the reaction was completed, OD$_{405}$ and OD$_{492}$ were measured, and the true optical density was obtained by OD$_{405}$ value-OD$_{492}$ value.

A blood sample was obtained from a mouse that had been injected intraperitoneally with 25 mg/ml of OVA in saline five times (once a week). From the blood sample, a serum sample was prepared as a standard serum. This standard serum was diluted 1/10 with PBS, and the resulting dilution was further diluted stepwise to twice with non-immunized serum to prepare working dilutions. These working dilutions were subjected to measurements of the coloring values in accordance with the above procedures, to obtain a working curve. Based on this working curve, the OVA-IgE levels in the serum samples were obtained as relative amounts with respect to the OVA-IgE level in the standard serum being as 1.

(Measurement of Total IgE in Blood)

50 μl of saline solution containing 10 μg/ml of a sheep polyclonal anti-mouse IgE antibody (trade name AAM11, manufactured by DAINIPPON PHARMACEUTICAL CO., LTD.) was added to each well of a 96-well immunoplate (manufactured by CORNING INCORPORATED), and incubated overnight at 4° C. The plate was washed three times with PBS, coated with 0.5% casein-PBS, and incubated for 3 hours at room temperature. After the plate was washed three times with PBS, 50 μl of a 1/25 dilution of a serum sample in 0.5% casein-PBS was added to each well, and reacted overnight at 4° C. After the plate was washed four times with PBS, 50 μl of a PBS solution containing 2 μg/ml of biotin-labeled anti-mouse IgE antibody (manufactured by YAMASA CORPORATION) and 0.5% casein was added to each well, and reacted for 2 hours at room temperature. After the plate was washed five times with 0.1%-Tween 20 in PBS, 50 μl of a PBS solution containing 1 μg/ml of streptavidin-peroxidase and 0.5% casein was added to each well, and reacted for 1 hour at room temperature. After the plate was washed five times with 0.1%-Tween 20 in PBS, 50 μl of 0.2 M citric acid buffer (pH5) containing 300 μg/ml of ABTS and 0.006% hydrogen peroxide was added to each well, and shielded for 20 to 30 minutes at room temperature for reaction. Then OD$_{405}$ was measured.

On the other hand, mouse anti-DNP-IgE (manufactured by YAMASA CORPORATION), instead of the serum samples, was dissolved in 0.5% casein-PBS at various concentrations, and subjected to the same procedures as above to obtain a working curve. Based on this working curve, the total IgE levels in the serum samples were calculated.

(Measurement of Total IgG in Blood)

50 µl of saline containing 1 µg/ml of goat anti-mouse IgG (H+L) antibody (trade name 62-6500, manufactured by ZYMED LABORATORIES, INC.) was added to each well of a 96-well immunoplate (manufactured by CORNING INCORPORATED), and incubated overnight at 4° C. The plate was washed three times with PBS, coated with 0.5% casein-PBS, and incubated for 3 hours at room temperature. After the plate was washed three times with PBS, 50 µl of a 1/1000 dilution of a serum sample in 5% casein-PBS was added to each well, and reacted overnight at 4° C. After the plate was washed four times with PBS, 50 µl of a PBS solution containing 2 µg/ml of peroxidase-labeled anti-mouse IgG(γ) antibody (manufactured by CAPPEL LABORATORIES, INC.) and 0.5% casein was added to each well, and reacted for 2 hours at room temperature. After the plate was washed five times with 0.1%-Tween 20 in PBS, 50 µl of 0.2 M citric acid buffer (pH5) containing 300 µg/ml of ABTS and 0.006% hydrogen peroxide was added to each well, and shielded for 20 to 30 minutes at room temperature for reaction. Then $OD_{405}$ was measured.

On the other hand, purified mouse IgG (manufactured by CAPPEL LABORATORIES, INC.), instead of the serum samples, was dissolved in 0.5% casein-PBS at various concentrations, and subjected to the same procedures as above to obtain a working curve. Based on this working curve, the total IgG levels in the serum samples were calculated.

Example 2

(Comparison in Effect of Various Lactic Acid Bacteria)

Each of the lactic acid bacterial strains shown in Table 1 was precultured in MRS medium overnight at 37° C., and the cells were harvested by centrifugation at 3000 rpm for 10 minutes. 9% (W/V) reconstituted skim milk (containing 0.1% (W/V) yeast extract (manufactured by DIFCO)) was fermented with the collected cells at 37° C. A until the milk was coagulated. After the fermentation, the total cell count of each fermented milk was measured. The results are shown in Table 1.

TABLE 1

| Strain | Total cell count (cells/ml) |
|---|---|
| Lactobacillus acidophilus CL92 (BP-4981) | $1.9 \times 10^8$ |
| Lactobacillus bulgaricus CP1812 | $1.5 \times 10^8$ |
| Lactobacillus fermentum CP34 | $5.3 \times 10^8$ |
| Lactobacillus helveticus CP790 | $2.4 \times 10^8$ |
| Lactobacillus johnsonii CP2551 | $2.7 \times 10^8$ |
| Lactobacillus plantarum CP2172 | $5.9 \times 10^8$ |
| Lactobacillus rhamnosus ATCC53103 | $1.0 \times 10^8$ |

Next, IgE-elevated mice were prepared in the same way as in Example 1, and the blood OVA-IgE was measured on day 18 of sensitization in the same way as in Example 1. The mice were divided into groups of 10 mice per group with the same average of blood OVA-IgE levels. From day 19 to 21 of sensitization, various fermented milks shown above, non-fermented 9% (W/V) reconstituted skim milk, or non-fermented 9 w/v % reconstituted skim milk containing 750 µg of cyclophosphamide were administered gastrically to each group of mice in dosages of 1 ml per day for three days. On day 22 of sensitization, blood samples from the mice were obtained from the ophthalmic veins, and serum samples were prepared. The blood OVA-IgE and the total IgG levels were measured. As a control, a blood sample from a mouse, which had been sensitized in the same way but given no fermented milk or the like, was obtained in the same way, and the blood OVA-IgE and the total IgG levels were measured. The results are shown in FIG. 2.

Figure 2:
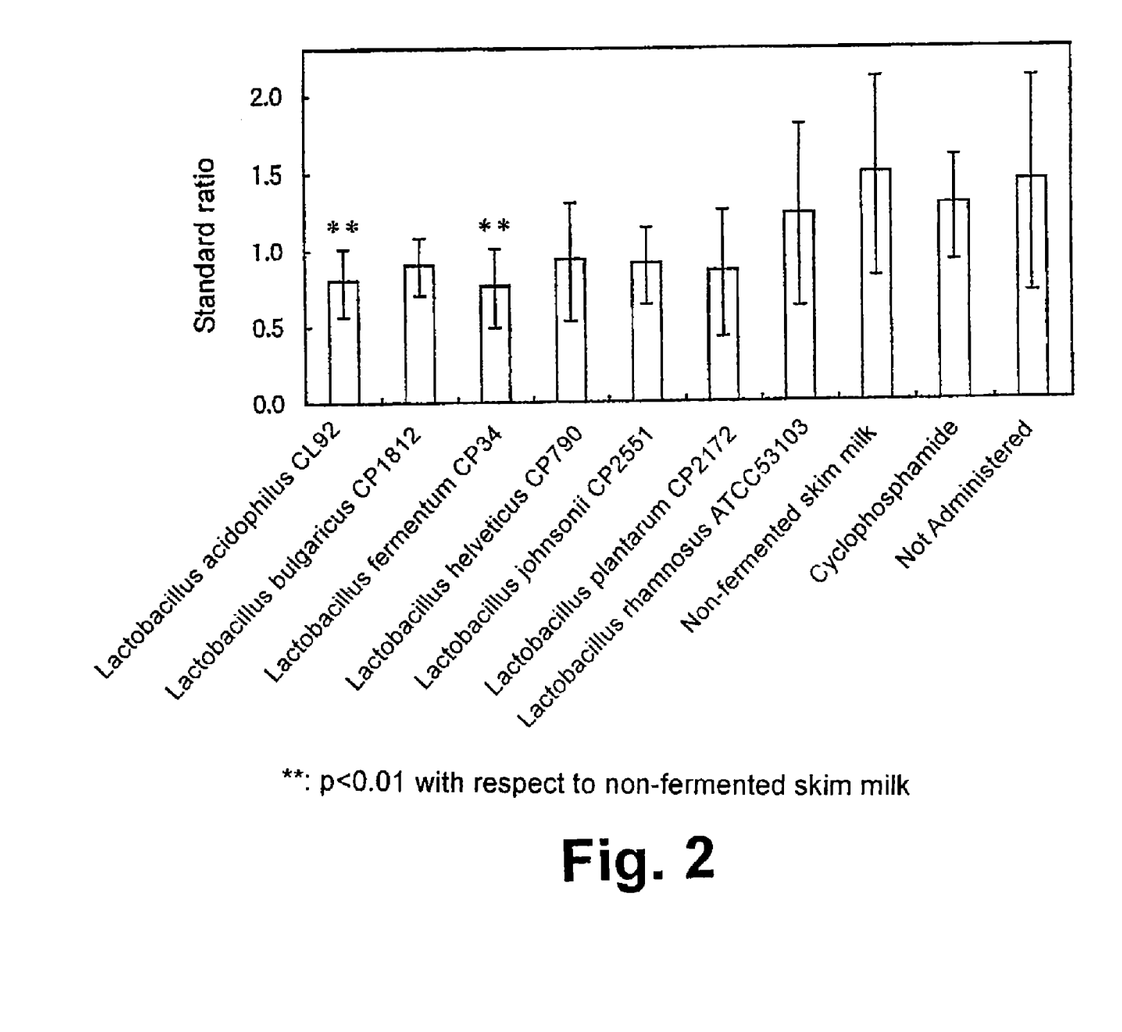
FIG. 2 is a graph showing the results of experiments for suppressing OVA-IGE level in IgE-elevated mice by administration of fermented milks, conducted in Example 2.

As shown in FIG. 2, in the groups of mice given *Lactobacillus acidophilus* or *Lactobacillus fermentum* fermented milk, significant inhibitory effect (p<0.01) in OVA-IgE level was observed, compared to the group given non-fermented skim milk. No significant difference was observed in total IgG level in blood (not shown).

Example 3

The procedure in Example 2 was followed except that the lactic acid bacterial strains shown in Table 2 were used. The results of measurement of the total cell count in each fermented milk are shown in Table 2. The results of measurement of the blood OVA-IgE are shown in FIG. 3.

TABLE 2

| Strain | Total cell count (cells/ml) |
|---|---|
| Lactobacillus acidophilus CL0062 (BP-4980) | $4.40 \times 10^8$ |
| Lactobacillus gasseri CP2209 | $4.30 \times 10^8$ |
| Lactobacillus reuteri ATCC23272 | $9.60 \times 10^8$ |
| Bifidobacterium breve CP2425 | $1.30 \times 10^8$ |

Figure 3:
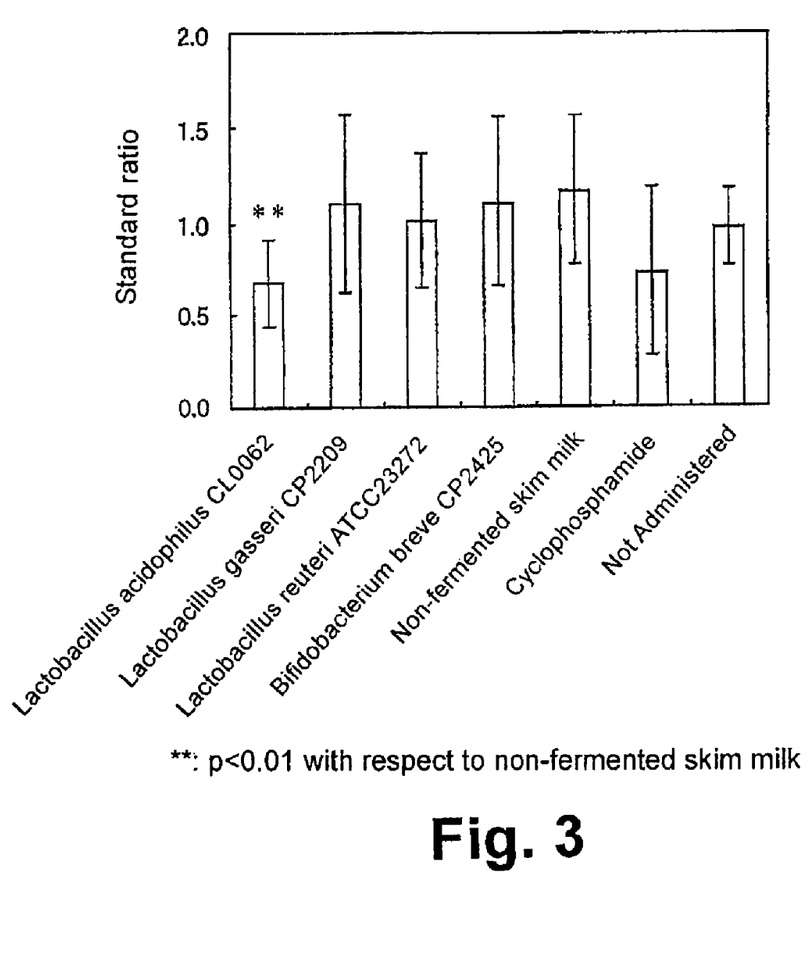
FIG. 3 is a graph showing the results of experiments for suppressing OVA-IgE level in IgE-elevated mice by administration of fermented milks, conducted in Example 3.

As shown in FIG. 3, in the group of mice given *Lactobacillus acidophilus* fermented milk, significant inhibitory effect (p<0.01) in OVA-IgE level was observed, compared to the group given non-fermented skim milk. No significant difference was observed in total IgG level in blood (not shown).

Example 4

(Confirmation of Effects in Lower Dosage)

*Lactobacillus acidophilus* CL92 strain and *Lactobacillus fermentum* CP34 strain were respectively precultured in MRS medium overnight at 37° C., and the cells were harvested by centrifugation at 3000 rpm for 10 minutes. The collected cells were cultured in MRS medium overnight at 37° C., and the cells were harvested by centrifugation at 3000 rpm for 10 minutes. The number of cells was measured for each strain, and the cells were suspended in 9% skim milk at a concentration of 1×10⁶ cells per 1 ml to obtain suspensions.

Next, IgE-elevated mice were prepared in the same way as in Example 1, and the blood OVA-IgE was measured on day 18 of sensitization in the same way as in Example 1. The mice were divided into groups of 10 mice per group with the same average of blood OVA-IgE levels. From day 19 to 21 of sensitization, the above suspensions were administered gastrically to each group of mice in dosages of 1 ml per day for three days. On day 22 of sensitization, blood samples from the mice were obtained from the ophthalmic veins, and serum samples were prepared. The blood OVA-IgE and the total IgG levels were measured. The results are shown in FIG. 4.

Figure 4:
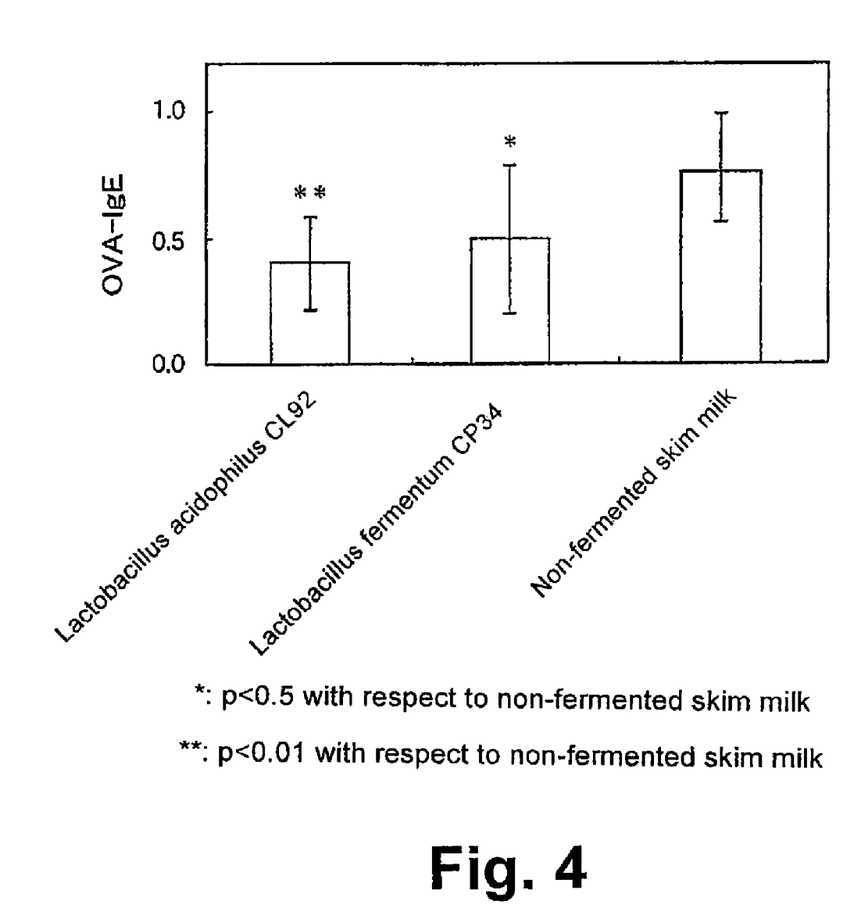
FIG. 4 is a graph showing the results of experiments for suppressing OVA-IgE level in IgE-elevated mice by administration of fermented milks, conducted in Example 4.

As shown in FIG. 4, in both groups of mice given *Lactobacillus acidophilus* CL92 strain or *Lactobacillus fermentum* CP34 strain, significant inhibitory effect in OVA-IgE level was observed, compared to the group given non-fermented skim milk. No significant difference was observed in total IgG level in blood (not shown).

The reduction rate d in OVA-IgE level when each suspension was administered is obtained by the formula d=1-(b/a), wherein a represents the standard ratio of OVA-IgE level when the non-fermented skim milk was fed, and b represents the standard ratio of OVA-IgE when each suspension was fed. Denoting the cell concentration of the suspension administered to mice by s (cells/ml), and assuming that s is in proportion to the reduction ratio d, the number of cells x (cells/ml) in the suspension required for reducing the OVA-IgE level by half in this experimental system is obtained by the formula x=(s×0.5)/d. Using this formula, the number of cells x for each bacterial strain used in Examples 2 and 3 was obtained. The results are shown in Table 3.

TABLE 3

| Strain | Number of cells required (cells/ml) |
| --- | --- |
| Lactobacillus acidophilus CL92 (BP-4981) | $1.0 \times 10^6$ |
| Lactobacillus bulgaricus CP1812 | $2.0 \times 10^8$ |
| Lactobacillus fermentum CP34 | $1.4 \times 10^6$ |
| Lactobacillus helveticus CP790 | $3.3 \times 10^8$ |
| Lactobacillus johnsonii CP2551 | $3.5 \times 10^8$ |
| Lactobacillus plantarum CP2172 | $7.0 \times 10^8$ |
| Lactobacillus rhamnosus ATCC53103 | $2.9 \times 10^8$ |
| Lactobacillus acidophilus CL0062 (BP-4980) | $5.0 \times 10^8$ |
| Lactobacillus gasseri CP2209 | $3.1 \times 10^9$ |
| Lactobacillus reuteri ATCC23272 | $3.3 \times 10^9$ |
| Bifidobacterium breve CP2425 | $1.1 \times 10^9$ |

Example 5

(Clinical Effect on Human)

Figure 5:
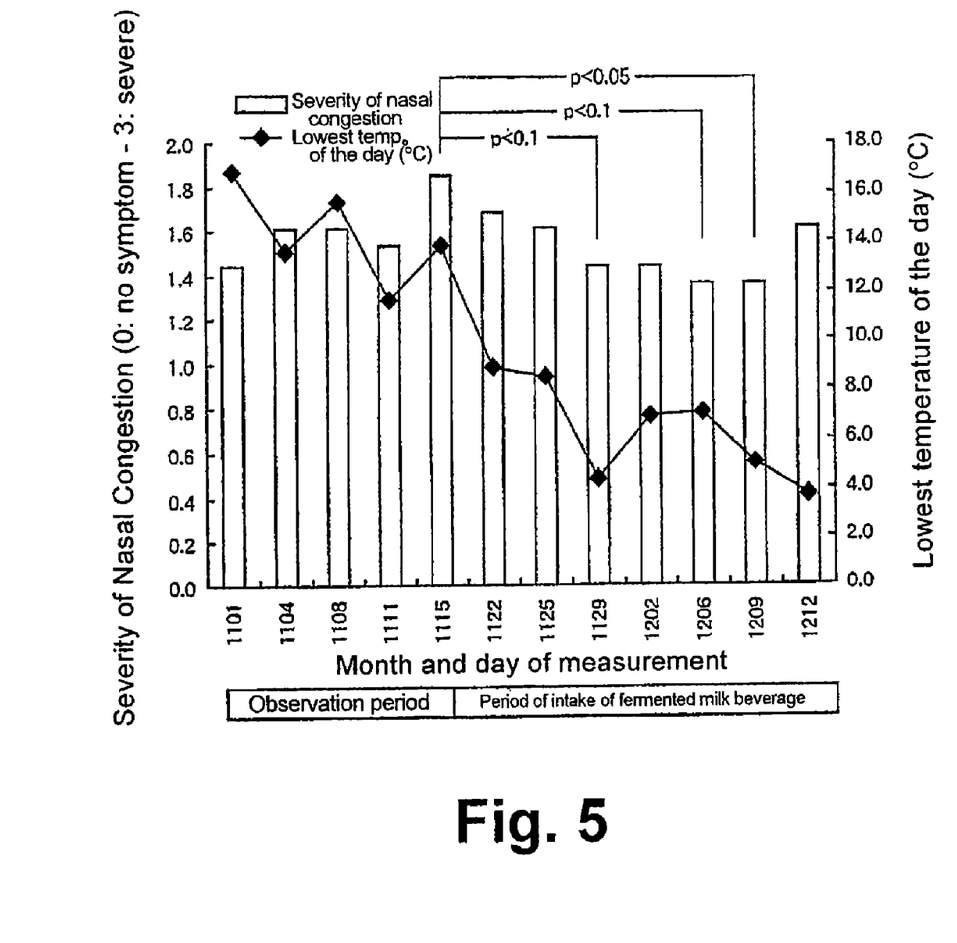
FIG. 5 is a graph showing the results of experiments for suppressing allergic symptoms in human by administration of fermented milk, conducted in Example 5.
Figure 6:
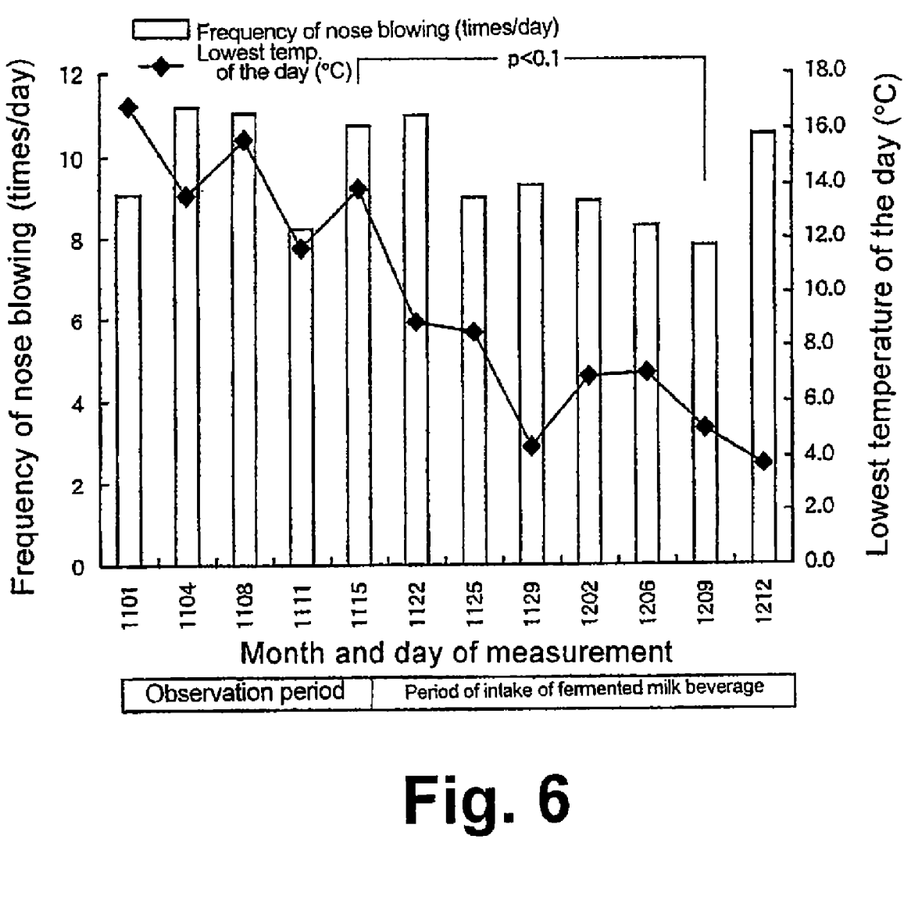
FIG. 6 is a graph showing the results of experiments for suppressing allergic symptoms in human by administration of fermented milk, conducted in Example 5.

Thirteen subjects suffering from perennial allergic rhinitis (average age 22.9±6.1 years old, 6 males and 7 females) were given, after 2 weeks of observation period, 100 ml/day of fermented milk containing $8.0 \times 10^8$ to $1.3 \times 10^9$ cells/ml of Lactobacillus acidophilus CL 92 strain for 4 weeks. Questionnaires on subjective symptoms were issued at intervals, and based on the responses the symptoms were scored in accordance with the "Severity Classification of Allergic Rhinitis" provided by Japanese Society of Allergology. Symptoms of rhinitis were diagnosed at intervals in accordance with the guideline of Japanese Society of Allergology. Blood samples were obtained from the subjects at intervals, and the IgE titers in blood were measured. Further, the lowest temperature of the day was recorded during the test period. Severity of nasal congestion of the subjects, frequency of nose blowing, and the lowest temperature of the day during the test period are shown in FIGS. 5 and 6.

During the test period, the lowest temperature of the day fluctuated greatly from 14° C. on the first day of intake (November 15) down to 3.7° C. on the last day of intake (December 13) over more than 10° C. Even under such conditions to deteriorate the rhinitis symptoms, nose congestion showed a tendency to improve two weeks after the commencement of intake (Wilcoxon test: p<0.1), and significant improve was observed four weeks after the commencement (Wilcoxon test: p<0.05). Frequency of nose blowing also showed a tendency to decrease three weeks after the commencement of intake (Wilcoxon test: p<0.1). During the period of intake, tendency of decrease in frequency of sneezing, remission of swelling of inferior nasal concha, and decrease in total IgE titer in blood were observed.

What is claimed is:

1. A method for reducing allergy comprising orally administering, to a human subject afflicted with the allergy, an effective dose of an antiallergic agent comprising, as an active ingredient, lactic acid bacteria of the strain Lactobacillus acidophilus CL92 (deposited at International Patent Organism Depositary, FERM BP-4981).

2. The method of claim 1, wherein administration of the lactic acid bacteria reduces elevated antigen-specific IgE levels in blood.

3. The method according to claim 1, wherein said lactic acid bacteria of the strain Lactobacillus acidophilus CL92 is either in live or killed form.

4. A method for reducing allergy comprising orally administering, to a human subject in need of such reduction, an effective dose of an antiallergic agent comprising, as an active ingredient, lactic acid bacteria of the strain Lactobacillus acidophilus CL92 (deposited at International Patent Organism Depositary, FERM BP-4981).

5. The method of claim 4, wherein administration of the lactic acid bacteria reduces elevated antigen-specific IgE levels in blood.

6. The method according to claim 4, wherein said lactic acid bacteria of the strain Lactobacillus acidophilus CL92 is either in live or killed form.

7. The method according to claim 2, wherein said elevated antigen-specific IgE levels in the blood is reduced without significant differnece in total IgG level.

8. The method according to claim 5, wherein said elevated antigen-specific IgE levels in the blood is reduced without significant difference in total IgG level.

9. A method for reducing elevated antigen-specific IgE levels in blood, said method comprising orally administering, to a human subject having an elevated antigen-specific IgE level in blood, an effective dose of an antiallergic agent comprising, as an active ingredient, lactic acid bacteria of the strain Lactobacillus acidophilus CL92 (deposited at International Patent Organism Depositary, FERM BP-4981).

10. The method according to claim 9, wherein said method for reducing elevated antigen-specific IgE levels in blood is a method for reducing elevated antigen-specific IgE levels in blood without significant difference in total IgG level.

11. The method according to claim 9, wherein said lactic acid bacteria of the strain Lactobacillus acidophilus CL92 is either in live or killed form.

* * * * *